(12) United States Patent  
Tsukagoshi

(10) Patent No.: US 7,031,423 B2
(45) Date of Patent: Apr. 18, 2006

(54) X-RAY COMPUTED TOMOGRAPHY APPARATUS AND PICTURE QUALITY SIMULATION APPARATUS

(75) Inventor: Shinsuke Tsukagoshi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 148 days.

(21) Appl. No.: 10/830,106

(22) Filed: Apr. 23, 2004

(65) Prior Publication Data

US 2005/0008115 A1    Jan. 13, 2005

(30) Foreign Application Priority Data

May 9, 2003    (JP)    ............................. 2003-131613

(51) Int. Cl.
*A61B 6/00* (2006.01)
(52) U.S. Cl. ............................. 378/4; 378/19; 378/901; 382/131
(58) Field of Classification Search ............ 378/4, 378/15, 19, 20, 91, 207, 901; 356/391; 382/128, 382/131; 353/28
See application file for complete search history.

(56) References Cited

U.S. PATENT DOCUMENTS 4,769,696 A * 9/1988 Utsuda et al. .............. 358/527
6,024,018 A * 2/2000 Darel et al. ................ 101/365
6,807,288 B1 * 10/2004 Inagaki ....................... 382/106
6,885,777 B1 * 4/2005 Inagaki ....................... 382/291
2002/0110268 A1 * 8/2002 Brinker et al. .............. 382/131

FOREIGN PATENT DOCUMENTS

JP    11-104121    4/1999
JP    11-235334    8/1999

* cited by examiner

*Primary Examiner*—Edward J. Glick
*Assistant Examiner*—Anastasia S. Midkiff
(74) *Attorney, Agent, or Firm*—Oblon, Spivak, McClelland, Maier & Neustadt, P.C.

(57) ABSTRACT

An X-ray computed tomography apparatus according to this invention includes a gantry (1) which scans an imaging target region of a subject to be examined in accordance with scan conditions, a reconstruction unit (36) which reconstructs image data from projection data, a scan plan setting support system (40) which sets scan conditions, an image SD calculating unit (41) which calculates an image SD associated with an index of picture quality on the basis of the set scan conditions, a data storage device (35) which stores sample image data having a reference value of an image SD, a simulation image generating unit (42) which generates simulation image data corresponding to the calculated image SD from the sample image data on the basis of the calculated image SD and the reference value of the image SD, and a display (38) which displays the generated simulation image data.

17 Claims, 8 Drawing Sheets

FIG. 3

| No. | SCAN MODE | Imaging range | Exposure reduction | CTDI(mGy) | kV | mA | Scan speed | Beam pitch | Bed speed | Function | Image slice thickness | FOV |
|---|---|---|---|---|---|---|---|---|---|---|---|---|
| 1 | Helical | 20.7 | OFF | 21.0 | 120 | 300 | 0.5 | 3.0 | 9.0 | FC10 | 5.0 | M |
|  |  |  |  |  |  |  |  |  |  |  |  |  |
|  |  |  |  |  |  |  |  |  |  |  |  |  |
|  |  |  |  |  |  |  |  |  |  |  |  |  |
|  |  |  |  |  |  |  |  |  |  |  |  |  |
|  |  |  |  |  |  |  |  |  |  |  |  |  |

Patient information

Gantry information

Scanogram

Main | Reconstruction condition | Window condition

Copy | Erase | Previous page | Check image SD | Confirm

FIG. 4

| Imaging region | | |
|---|---|---|
| Chest | | |
| Body thickness | | |
| 25.0 cm | | |
| Water equivalent thickness | | |
| 29.5 cm | | |
| Imaging range | | |
| 20.7 cm | | |
| Imaging time | | |
| 11.5 sec | | |

Exposure reduction: OFF
FOV: M
Function: FC10

Scan mode: Helical Scan
Image slice thickness: 5.0 mm
Imaging slice thickness: 3.0 mm
Pitch: 3.0
Bed speed: 9.0 mm / rotation
Scan speed: 0.5 sec / rotation
kV: 120
mA: 300

Display simulation image

SD — CTDI —

Result
Image SD:
Dose
CTDI [mGy]: 21.0
DLP [mGy·cm]: 509.1

Reflect    Close

X-RAY COMPUTED TOMOGRAPHY APPARATUS AND PICTURE QUALITY SIMULATION APPARATUS

CROSS-REFERENCE TO RELATED APPLICATIONS

This application is based upon and claims the benefit of priority from the prior Japanese Patent Application No. 2003-131613, filed May 9, 2003, the entire contents of which are incorporated herein by reference.

BACKGROUND OF THE INVENTION

1. Field of the Invention

The present invention relates to an X-ray computed tomography apparatus and picture quality simulation apparatus.

2. Description of the Related Art

As is known, an X-ray computed tomography apparatus is designed to obtain an image (tomographic image) by calculating (reconstructing) the X-ray absorption coefficient of a tissue such as an organ on the basis of the amount of X-rays absorbed in a subject to be examined as an index called a CT value with reference to the X-ray absorption coefficient of water. A reconstructed image inevitably contains image noise. Image noise is typically defined with reference to a variation in the CT value of a homogeneous phantom image as a standard deviation, which is generally abbreviated as an image SD.

An image SD is determined in accordance with a plurality of condition items such as an imaging slice thickness, tube voltage, and tube current in scanning conditions, and a subject to be examined. In order to make diagnosis by observing a reconstructed image, e.g., to discriminate a small shadow on the image as noise or a tumor, the image SD of the image must be considered. In other words, scan condition items such as an imaging slice thickness, tube voltage, and tube current must be set to set the image SD to a proper value that allows discrimination between a tumor to be examined and noise.

As disclosed in Jpn. Pat. Appln. KOKAI Publication No. 11-235334, it is difficult to grasp the value of image SD only by inputting many condition items such as an imaging slice thickness, tube voltage, and tube current. In addition, even if an image SD can be grasped, many experiences and knowledge are required to recognize how much noise will occur with respect to the value of image SD. This is not an easy operation. It is therefore difficult to suitably set scan conditions.

BRIEF SUMMARY OF THE INVENTION

It is an object of the present invention to provide an X-ray computed tomography apparatus and a picture quality simulation apparatus which can set scan conditions more suitably.

According to a first aspect of the present invention, there is provided an X-ray computed tomography apparatus comprising a scan unit configured to scan an imaging target region of a subject to be examined with X-rays in accordance with a scan condition, a reconstruction unit configured to reconstruct image data on the basis of projection data acquired by the scan, a scan condition setting unit configured to set the scan condition, a picture quality index calculating unit configured to calculate a value associated with an index of picture quality on the basis of the set scan condition, a sample image storage unit configured to store sample image data corresponding to a reference value associated with the index of picture quality, a simulation image generating unit configured to generate simulation image data corresponding to the calculated value associated with the index of picture quality from the sample image data on the basis of the calculated value associated with the index of picture quality and the reference value associated with the index of picture quality, and a display unit configured to display the generated simulation image data.

According to a second aspect of the present invention, there is provided an X-ray computed tomography apparatus comprising a scan unit configured to scan an imaging target region of a subject to be examined with X-rays, a reconstruction unit configured to reconstruct image data on the basis of projection data acquired by the scan, an input unit configured to input a value or dose associated with an index of picture quality, a simulation image generating unit configured to generate simulation image data corresponding to the input value or dose associated with the index of picture quality, and a display unit configured to display the generated simulation image data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a view showing an example of a scan plan setting window displayed in step S2 in FIG. 2;

FIG. 4 is a view showing an example of an image SD check window displayed in step S5 in FIG. 2;

FIG. 8 is a view showing an example of a display window displayed by a picture quality simulation apparatus according to the embodiment of the present invention.

DETAILED DESCRIPTION OF THE INVENTION

An X-ray computed tomography apparatus according to an embodiment of the present invention will be described below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements arrayed in the form of a ring, and only an X-ray tube rotates around a subject to be examined. The present invention can be applied to either type. In this case, the rotate/rotate type, which is currently the mainstream, will be exemplified. In order to reconstruct one-slice tomographic image data, projection data corresponding to one rotation around a subject to be examined, i.e., about 360°, is required, or (180°+ view angle) projection data is required in the half scan method. The present invention can be applied to either of these reconstruction schemes. The former scheme will be exemplified here. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomography apparatus having a plurality of pairs of X-ray tubes and X-ray detectors mounted on a rotating ring, related techniques have been developed. The present invention can be applied to both a conventional single-tube type X-ray computed tomography apparatus and a multi-tube type X-ray computed tomography apparatus. The single-tube type X-ray computed tomography apparatus will be exemplified here.

Figure 1:
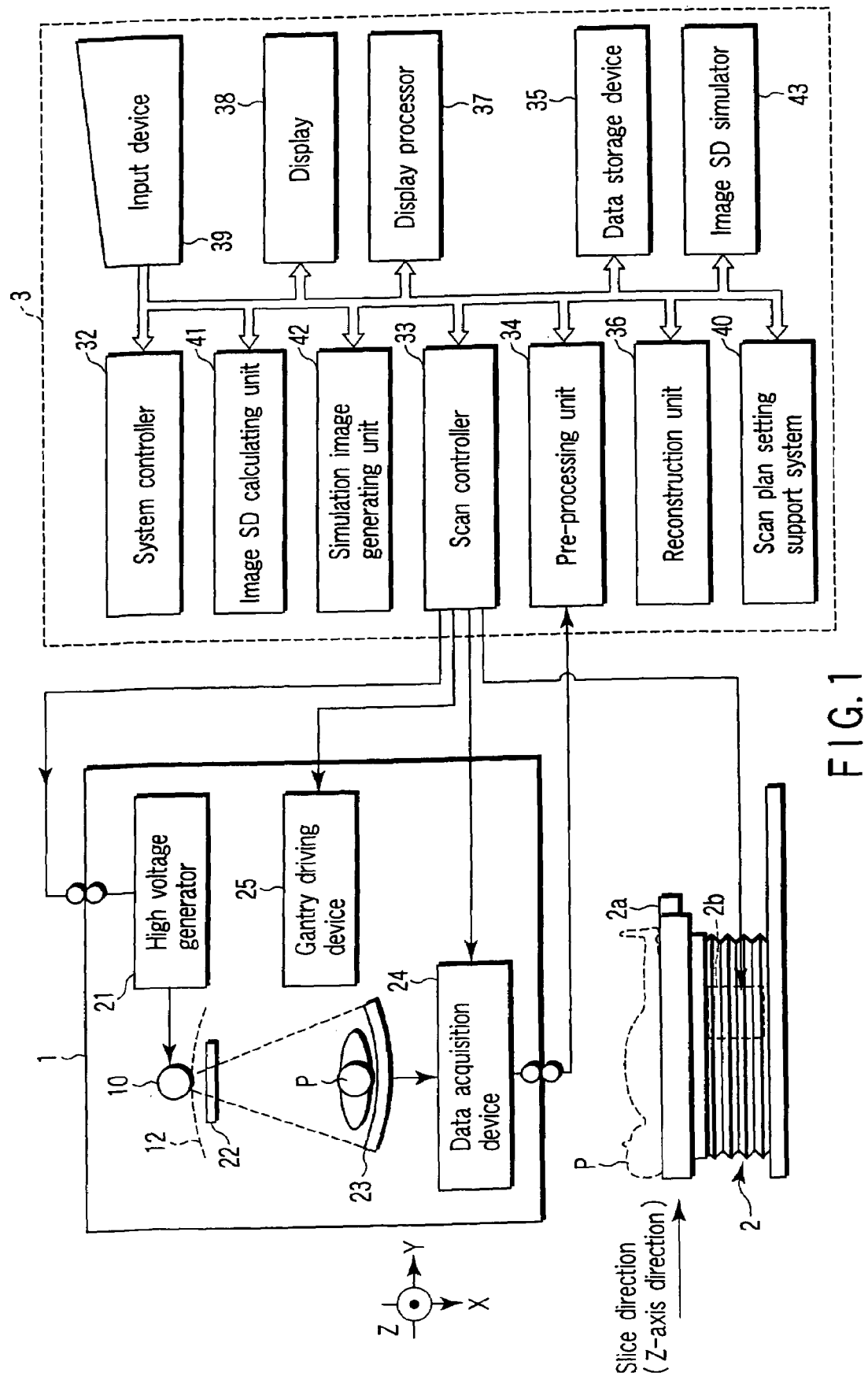
FIG. 1 is a view showing the arrangement of an X-ray computed tomography apparatus according to an embodiment of the present invention.

FIG. 1 shows the arrangement of an X-ray computed tomography apparatus according to this embodiment. A gantry 1 has an X-ray tube 10 and X-ray detector 23. The X-ray tube 10 and X-ray detector 23 are mounted on an annular rotating frame 12 so as to face each other. The rotating frame 12 is rotated about the Z-axis by a gantry driving device 25. An opening portion is formed in the central portion of the rotating frame 12. A subject P to be examined which is placed on a top 2a of a bed 2 is inserted in the opening portion. A slit 22 for changing the radiation width of X-rays in accordance with a beam pitch (also referred to as an imaging slice width) is placed between the X-ray tube 10 and the opening portion. The bed 2 is equipped with a top driving unit 2b for moving the top 2a in the direction of the long axis (parallel to the rotation axis) of the top.

A high voltage generator 21 applies a tube voltage between the cathode and the anode of the X-ray tube 10. The high voltage generator 21 also supplies a filament current to the filament of the X-ray tube 10. X-rays are generated by the application of the tube voltage and the supply of the filament current. In order to realize high-speed continuous rotation, the X-ray tube 10 is electrically connected to the high voltage generator 21 through a slip ring.

The X-ray detector 23 is a single slice type detector or multi-slice type detector. The X-ray detector 23 as a single slice type detector has an element array of, for example, 916 X-ray detection elements, each having a 0.5 mm×0.5 mm square light-receiving surface, arranged in a line along a channel direction Y. The X-ray detector 23 as a multi-slice type detector has, for example, 40 element arrays arranged side by side in a slice direction Z.

A data acquisition device 24 generally called a DAS (Data Acquisition System) converts a signal output from the X-ray detector 23 for each channel into a voltage signal, amplifies it, and further converts it into a digital signal. This data (raw data) is loaded into a computer unit 3 placed outside the gantry. A pre-processing unit 34 of the computer unit 3 performs correction processing such as sensitivity correction for the raw data output from the data acquisition device 26 and outputs the resultant projection data. This projection data is sent to a data storage device 35 of the computer unit 3 to be stored.

In addition to the pre-processing unit 34 and data storage device 35, the computer unit 3 is comprised of a system controller 32, an input device 39 including a keyboard, mouse, and the like, a display 38, a display processor 37, a scan controller 33, a reconstruction unit 36, a scan plan setting support system 40, an image SD calculating unit 41, a simulation image generating unit 42, and an image SD simulator 43. The reconstruction unit 36 reconstructs image (tomographic image) data on the basis of the projection data stored in the data storage device 35. The data storage device 35 stores the projection data generated by the pre-processing unit 34 and the tomographic image data reconstructed by the reconstruction unit 36, and also stores in advance sample image data to be used by the simulation image generating unit 42 to generate simulation image data.

The sample image data is obtained by actually scanning a phantom which faithfully reproduces the internal tissues of the human body or a subject to be examined which consents the use of itself as a sample image. This data has a predetermined image SD corresponding to scan conditions at the time of this scan operation. Note that the image SD which this sample image has will be referred to as a reference image SD. The simulation image generating unit 42 generates image data (simulation image data) having noise equivalent to the image SD calculated by the image SD calculating unit 41 from the sample image data on the basis of the image SD calculated by the image SD calculating unit 41 on the basis of the scan conditions and the like, set by the scan plan setting support system 40, and the reference image SD which the sample image data has. The processing time required to generate simulation image data from sample image data can be made much shorter than the processing time required to reconstruct simulation image data by processing sample projection data on the basis of an image SD. This makes it feasible to perform the processing of checking an image SD on an actual image and the processing of correcting the corresponding scan conditions when setting scan conditions. The processing of generating simulation image data from sample image data will be described below, together with the processing of setting scan conditions.

As written on the lower left column in FIG. 4, scan conditions typically include a scan mode, ON/OFF of an exposure reducing function, an imaging slice thickness (an X-ray thickness corresponding to a single slice on a rotation center axis), an image slice thickness (reconstruction slice thickness), an FOV (reconstruction field of view), a helical pitch (the moving distance of the bed per rotation), a bed speed, a reconstruction function, a tube voltage (kV), a tube current (mA), and a scan speed (the time required for one rotation).

Figure 2:
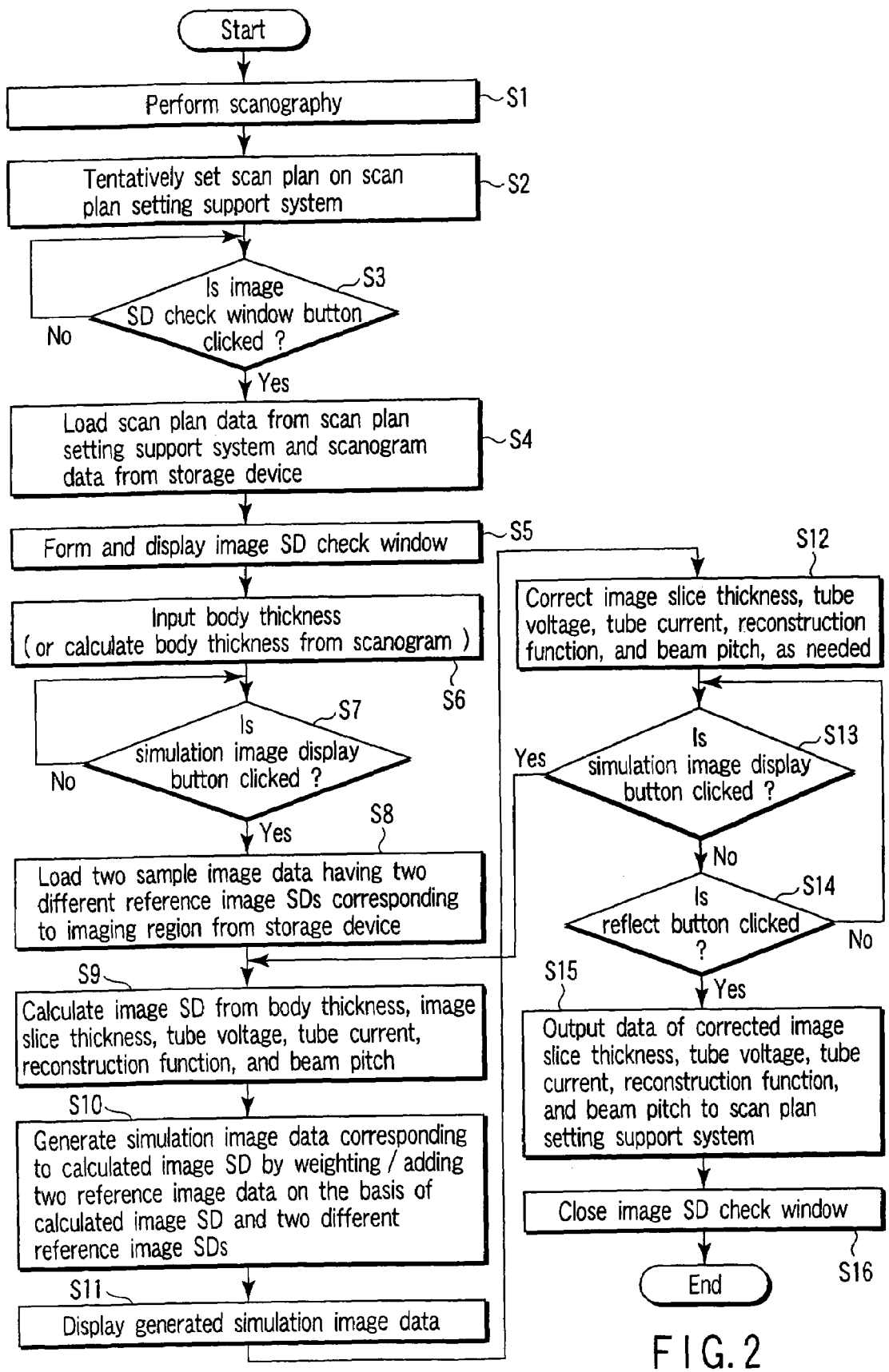
FIG. 2 is a flowchart showing an example of an operation sequence in this embodiment.

FIG. 2 shows a typical flow of processing in a case wherein the processing of generating simulation image data from sample image data is used in the processing of setting scan conditions in this embodiment. In S1, a scanogram of the entire or part of the body of a subject to be examined is taken. As is known, in scanography, for example, the X-ray tube 10 continuously irradiates the subject with X-rays while the rotating frame 12 is fixed at an angle of 0° at which it faces the subject on the top 2a or the top 2a is continuously moved at a predetermined speed, together with the subject, and X-rays transmitted through the subject are repeatedly detected by the X-ray detector 23 in a predetermined cycle. This makes it possible to generate image data similar to an X-ray planar image, i.e., scanogram data.

Scan conditions are then set. This setting is made by the support of the scan plan setting support system 40. The scan plan setting support system 40 has a function necessary to facilitate setting of scan conditions by the operator in an interactive manner. If, for example, the operator inputs items such as patient information, examination purpose, and examination target region, the scan plan setting support system 40 generates and presents at least one scan condition candidate corresponding to the input items.

Note that when the operator inputs an image SD, the scan plan setting support system 40 may generate and present at least one scan condition candidate to achieve the input image SD. Alternatively, when the operator inputs a dose value (CTDI), the scan plan setting support system 40 may create and present at least one scan condition candidate to achieve the input CTDI.

FIG. 3 shows a scan condition setting support window formed by the scan plan setting support system 40. Patient information, gantry information, and a scanogram are displayed on the scan condition setting support window, together with a scan condition candidate list below them. The main condition items included in scan conditions include a scan mode (single slice scan, multi-slice scan, and helical scan), an imaging range, a tube voltage, a tube current, a scan speed representing the time required for one rotation of the X-ray tube 10, a beam pitch representing the ratio of the moving distance of the top per rotation of the X-ray tube 10 to an X-ray beam width in helical scan, a bed speed representing the moving distance of the top per rotation of the X-ray tube 10 in helical scan, an imaging slice thickness, a reconstruction function, an image slice thickness, an S-FOV representing the diameter of an imaging area, a D-FOV representing the diameter of a reconstruction area, and the like. A radiographer selects a desired candidate from the presented scan condition candidates, and corrects the candidate values in desired condition items as needed, thereby effortlessly setting scan conditions.

The scan condition setting support window includes a button written as "check image SD". If the "check image SD" button is clicked in S3, the image SD simulator 43 is activated. The image SD simulator 43 loads the set scan plan data from the scan plan setting support system 40, and also loads scanogram data from the data storage device 35 (S4). The image SD simulator 43 forms the image SD check window shown in FIG. 4 from the loaded scan plan data and scanogram data, and displays the window (S5).

As shown in FIG. 4, the image SD check window includes a scanogram display area at the upper left portion, a simulation image display area at the upper right portion, an imaging region display box, a body thickness display box, a water equivalent thickness display box, an imaging range display box, an imaging time display box, a scan mode display box, an exposure reducing display box, an imaging slice thickness display box, an image slice thickness display box, an FOV display box, a beam pitch (Pitch) display box, a bed speed display box, a reconstruction function (function) display box, a tube voltage (kV) display box, a tube current (mA) display box, a scan speed display box, an image SD display box, a dose amount (CTDI, DLP) display box, and a window level/window width display box. In these display boxes, except for the body thickness display box, water equivalent thickness display box, and image SD display box, region names or numerical values of the corresponding items included in the scan plan data are initially entered.

A body thickness is numerically input on the image SD check window through the input device 39. Alternatively, a body thickness is calculated by the image SD simulator 43 from scanogram data. A water equivalent thickness is calculated by the image SD simulator 43 from the input or calculated body thickness. Alternatively, a water equivalent thickness is directly calculated by the image SD simulator 43 from scanogram data. There are various methods of calculating a water equivalent thickness from a body thickness; an arbitrary method can be used. According to an example of a method of calculating a water equivalent thickness from a body thickness, the water equivalent thickness of the subject is estimated from the diameter of a water phantom on the basis of the ratio of a pixel value in a scanogram of the subject to the pixel value of the pre-acquired scanogram of a cylindrical water phantom having a known diameter. In practice, in order to reduce an error, the water equivalent thickness of the subject is estimated by multiplying the diameter of the water phantom by the square root of the ratio of the pixel value integral of a local area in a scanogram of the subject to the pixel value integral of a local area of the same size in a scanogram of a cylindrical water phantom having a known diameter.

The image SD check window includes a button written as "display simulation image". When the "display simulation image) button is clicked in S7, sample image data is also loaded from the data storage device 35 into the simulation image generating unit 42 under the control of the image SD simulator 43 (S8). In practice, the data of a plurality of (two in this case) sample images are associated with each of a plurality of regions in the data storage device 35. The two sample images associated with the same region have different image SDs. For example, one sample image (first sample image) has an image SD (first reference image SD) of 2.0, and the other sample image (second sample image) has an image SD (second reference image SD) of 50.0. As is known, the smaller the image SD, the higher the picture quality, and vice versa.

In S9, the image SD calculating unit 41 calculates an image SD as an index of image noise on the basis of the set value of a specific condition item in the scan plan and the calculated water equivalent thickness. There are various methods of calculating an image SD; an arbitrary method can be used. For example, an image SD is calculated by the following method.

Figure 5A:
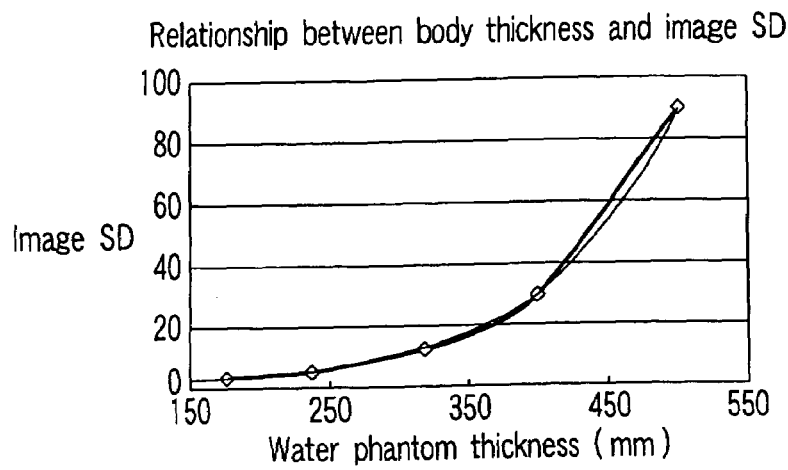
FIGS. 5A to 5E are graphs for additionally explaining image SD calculation processing in step S9 in FIG. 2.
Figure 5B:
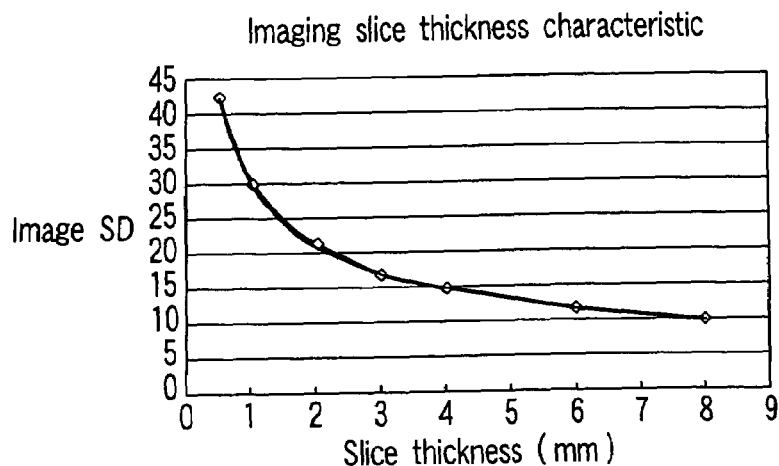
Figure 5C:
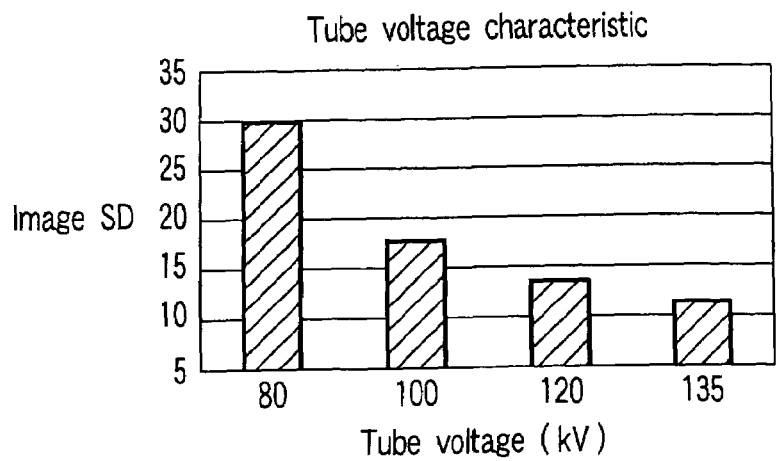
Figure 5D:
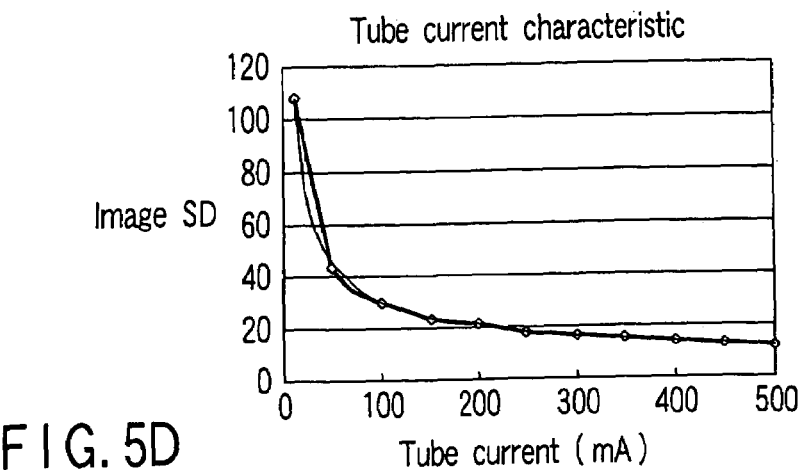
Figure 5E:
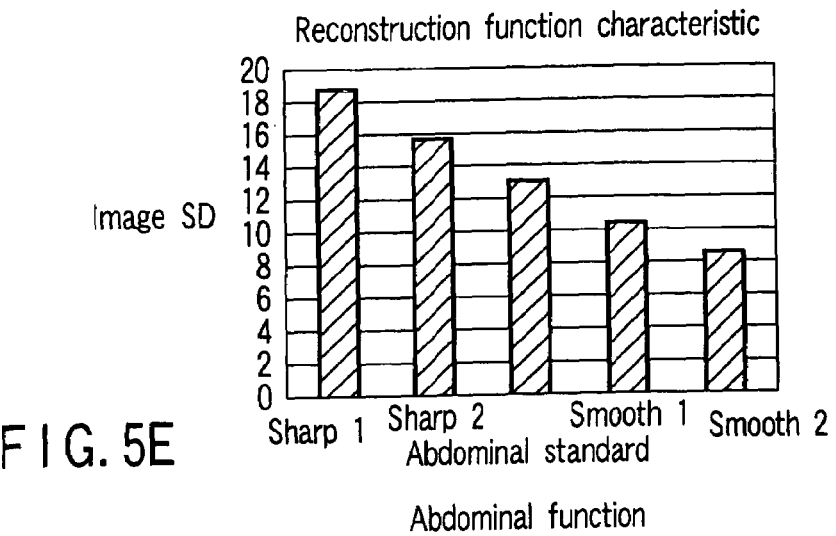

In this method, an image SD is obtained on the basis of an imaging slice thickness, tube voltage, tube current, reconstruction function, beam pitch, and water equivalent thickness. As a relationship between a water equivalent thickness and an image SD, a relationship between a water phantom thickness and an image SD is obtained according to an exponential approximate expression by sequentially scanning a plurality of types (e.g., five types) of water phantoms having different diameters while all the condition items of scan conditions are fixed to reference values, and obtaining the image SDs of the respective images, as shown in FIG. 5A. The corresponding approximate expression data is stored in the data storage device 35 in advance. A relationship between an imaging slice thickness and an image SD is obtained according to an approximate expression by repeatedly scanning a specific water phantom with different imaging slice thicknesses while the remaining condition items of the scan conditions are fixed to reference values, and obtaining the image SDs of the respective images, as shown in FIG. 5B. The corresponding approximate expression data is stored in the data storage device 35 in advance. A relationship between a tube voltage and an image SD is obtained according to an approximate expression by repeatedly scanning a specific water phantom with different tube voltages while the remaining condition items of the scan conditions are fixed to reference values, and obtaining the image SDs of the respective images, as shown in FIG. 5C. The corresponding approximate expression data is stored in the data storage device 35 in advance. A relationship between a tube current and an image SD is obtained according to an approximate expression by repeatedly scanning a specific water phantom with different tube currents while the remaining condition items of the scan conditions are fixed to reference values, and obtaining the image SDs of the respective images, as shown in FIG. 5D. The corresponding approximate expression data is stored in the data storage device 35 in advance. A relationship between a beam pitch and an image SD is obtained according to an approximate expression by repeatedly scanning a specific water phantom with different beam pitches while the remaining condition items of the scan conditions are fixed to reference values, and obtaining the image SDs of the respective images. The corresponding approximate expression data is stored in the data storage device 35 in advance. A relationship between a reconstruction function and an image SD is obtained according to an approximate expression by repeatedly scanning a specific water phantom once while all the condition items of the scan conditions are fixed to reference values, repeatedly performing image reconstruction with different reconstruction functions, and obtaining the image SDs of the respective images. The corresponding approximate expression data is stored in the data storage device 35 in advance.

The image SD calculating unit 41 specifies image SD values corresponding to the respective set values of condition items (an imaging slice thickness, tube voltage, tube current, beam pitch, and reconstruction function) corresponding to the scan conditions set on the scan plan setting support system 40 and the body thickness of an imaging target region of the subject from these five types (six types in helical scan) of approximation expression data, and multiplies the values obtained by normalizing the specified image SD values with corresponding normalization coefficients, thereby scanning the imaging target region of the subject with the set values of the scan condition items. An image is then reconstructed from the resultant projection data by using the selected reconstruction function, and the image SD value of the image is calculated, or in practice, estimated.

Figure 6:
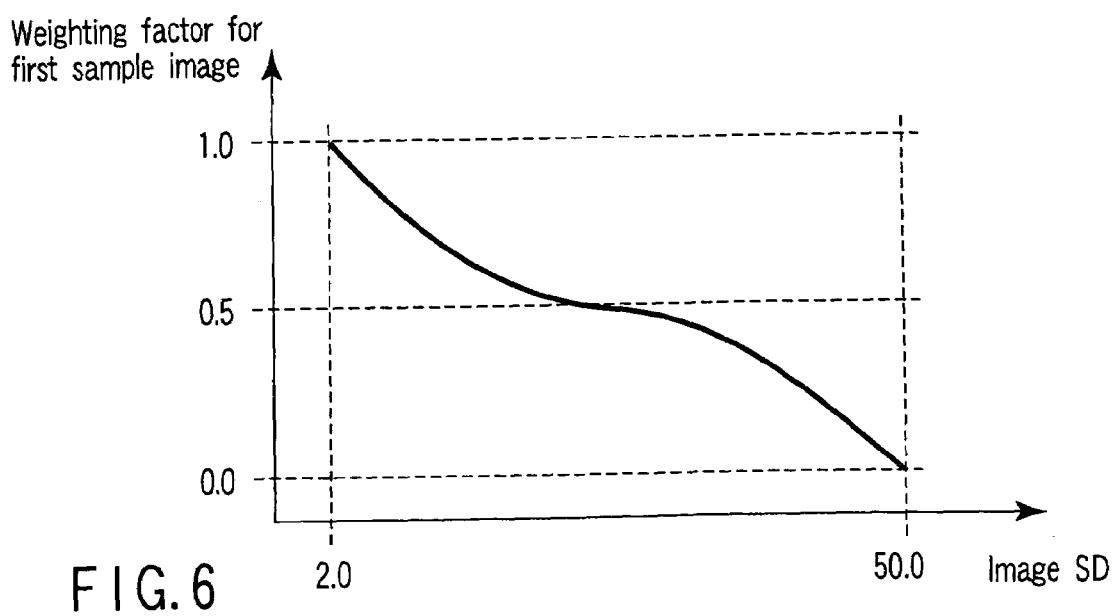
FIG. 6 is a view showing an example of a method of determining weighting factors for two sample images in step S10 in FIG. 2.

In S10, on the basis of the image SD calculated by the image SD calculating unit 41, the simulation image generating unit 42 generates an image (simulation image) having noise equivalent to the image SD from the sample image data. The simulation image generating unit 42 generates simulation image data by interpolating two types of sample image data loaded from the data storage device 35, which are associated with the imaging target region and have different image SDs, in accordance with the positions of the calculated image SDs corresponding to the interval between the first and second reference image SDs. As is known, interpolation processing is the processing of multiplying pixel values at positions corresponding to the first and second sample images by the first and second weighting factors, and adding the products. The values of the first and second weighting factors are determined such that the sum becomes 1.0. The respective values may be determined by a method complying with so-called simple distance interpolation processing, i.e., determining the ratio of the distance between the first reference image SD and a calculated image SD to the distance between the first and second reference image SDs as the first weighting factor by which the first sample image is to be multiplied, and determining the ratio of the distance between the second reference image SD and the calculated image SD to the distance between the first and second reference image SDs as the second weighting factor by which the second sample image is to be multiplied. Alternatively, these values may be determined in accordance with a predetermined multi-degree function, as shown in FIG. 6.

Generating simulation image data from two types of sample image data having different reference image SDs in this manner can shorten the processing time. Although an example of generating simulation image data from two types of sample image data has been described above, simulation image data may be generated by adding noise equivalent to the ratio between a reference image SD corresponding to high picture quality, e.g., 2.0, and a calculated image SD to one type of sample image data having the reference image SD. In contrast to this, simulation image data may be generated by performing noise reduction equivalent to the ratio between a reference image SD corresponding to low picture quality, e.g., 50.0, and a calculated image SD with respect to one type of sample image data having the reference image SD. Alternatively, simulation image data may be generated from three or more types of sample image data having three or more different reference image SDs by interpolation with weighting factors corresponding to the ratios between the respective reference image SDs and calculated image SDs.

Figure 7:
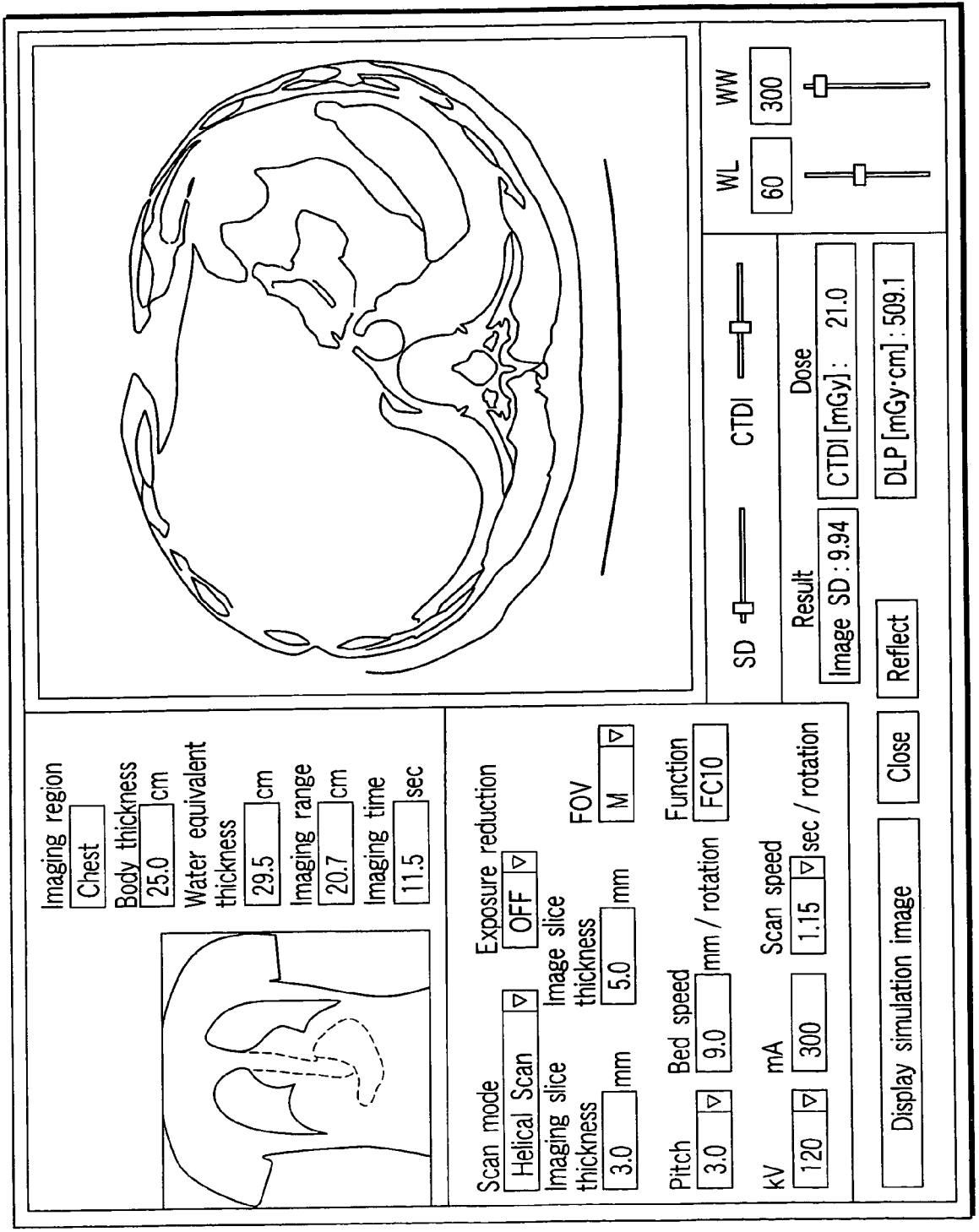
FIG. 7 is a view showing an example of a simulation image display window displayed in step S11 in FIG. 2.

The image SD simulator 43 then forms and displays the image SD check window shown in FIG. 7 which includes the image SD calculated by the image SD calculating unit 41 and the simulation image generated by the simulation image generating unit 42 (S11).

The radiographer corrects the set values of an imaging slice thickness, tube voltage, tube current, reconstruction function, and beam pitch through the input device 39, as needed (S12). If the "display simulation image" button is clicked in S13 after the correction, the flow returns to S9, in which the image SD calculating unit 41 re-calculates an image SD on the basis of the corrected values of the scan condition items, the uncorrected set values of the scan condition items in the scan plan, and the calculated water equivalent thickness. In S10 and S11, the simulation image generating unit 42 generates simulation image data corresponding to the re-calculated image SD from the same sample image data on the basis of the image SD re-calculated by the image SD calculating unit 41 within a short period of time, and displays the simulation image data.

Upon checking the result, the radiographer re-corrects the imaging slice thickness, tube voltage, tube current reconstruction function, and beam pitch, as needed (S12). By repeating the processing from S8 to S13, the radiographer can approximate the imaging slice thickness, tube voltage, tube current, reconstruction function, and beam pitch to optimal values while visually checking the image SD and the degree of noise corresponding to the image SD on the simulation image. Optimal values are defined as values which allow clear recognition of an examination target such as a tumor without blurring by noise and can minimize exposure.

When a button written as "reflect" is clicked in the image SD check window (S14), corrected value data of the imaging slice thickness, tube voltage, tube current, reconstruction function, and beam pitch are supplied to the scan plan setting support system 40 under the control of the image SD simulator 43 (S15). The scan plan setting support system 40 replaces the values of the corresponding items of the scan plan with the supplied corrected values of the imaging slice thickness, tube voltage, tube current, reconstruction function, and beam pitch. When the "confirm" button in FIG. 3 is clicked, the corrected values of the imaging slice thickness, tube voltage, tube current, reconstruction function, and beam pitch, which are corrected on the image SD check window, are confirmed as the set values of the scan conditions. When the "close" button in FIG. 7 is clicked, the image SD check window is closed (S16).

Note that the radiographer can set a desired image SD by directly inputting an image SD as a numerical value or moving a slider button on the window shown in FIG. 4, as needed. When the radiographer sets a desired image SD and clicks the simulation image display button, the flow returns to S10, in which the image SD simulator 43 generates a simulation image corresponding to the set image SD, and displays it. The radiographer can display a simulation image corresponding to an arbitrary image SD and easily check the degree of noise.

In addition, the radiographer can set a desired CTDI by directly inputting a dose, typically a CTDI, as a numerical value, or moving a slider button, as needed. When the radiographer sets a desired CTDI and clicks the simulation image display button, the image SD simulator 43 postulates scan conditions for realizing the set CTDI, calculates an image SD in S9, and generates and displays a simulation image corresponding to the image SD in S10. The radiographer can display a simulation image corresponding to an arbitrary dose (CTDI) and easily check the degree of noise.

Figure 8:
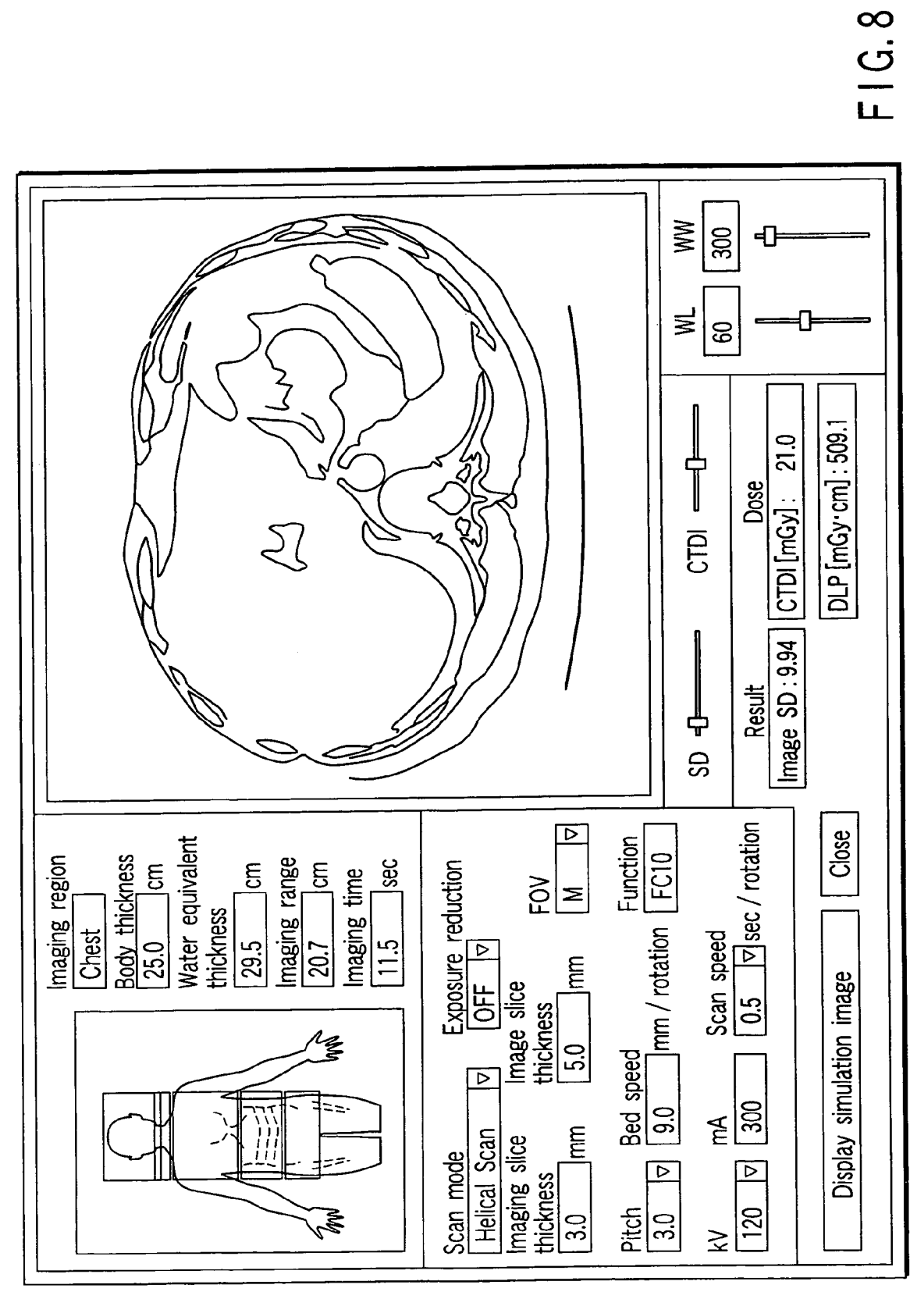

Note that the picture quality simulation apparatus including the data storage device 35 which stores the above sample image data, the image SD calculating unit 41, the simulation image generating unit 42, the display processor 37, the display 38, and the input device 39 may be provided independently of the X-ray computed tomography apparatus. As shown in FIG. 8, an image SD simulation window is displayed. On this simulation window, the body thickness, water equivalent thickness, scan mode, ON/OFF of exposure reduction, imaging slice thickness, image slice thickness, FOV, beam pitch, bed speed, reconstruction function, tube voltage, tube current, and scan speed are set to arbitrary values, and the "display simulation image" button is clicked, thereby displaying a simulation image having an image SD corresponding to the set values and a noise level corresponding to the image SD almost in real time. When a head portion, chest portion, abdominal portion, or lower limb portion is selected on a body mark of the scanogram displayed in the upper left area in the window, the current image is switched to a simulation image of the selected region almost in real time. The picture quality simulation apparatus may be used as follows. Placing this apparatus near the console of an X-ray computed tomography apparatus having no picture quality simulation apparatus can approximate scan conditions to optimal values upon reception of support of a picture quality simulation, like a most advanced apparatus having the above function. In addition, the picture quality simulation apparatus can be used as teaching equipment for a will or radiographer with little experiment. In addition, since the picture quality simulation apparatus is physically separated from the X-ray computed tomography apparatus, and picture quality simulation apparatus can be used in various scenes.

In addition, this embodiment may be provided as a computer-readable storage medium on which program codes for causing a computer to realize the processing sequence in FIG. 2 are recorded.

According to the above description, when scan conditions or an imaging region are input, a corresponding image SD is calculated, and a simulation image corresponding to the calculated image SD is generated and displayed. However, when, for example, a doctor or radiographer directly inputs a desired image SD together with an imaging region, a simulation image corresponding to the input image SD may be generated and displayed from sample image data corresponding to the input imaging region on the basis of the image SD reference value of the sample image data and the input desired image SD in the same manner as described above. In addition, a plurality of recommended values associated with scan conditions may be stored in the data storage device 35 in association with a plurality of imaging regions and image SDs, and recommended values of scan conditions corresponding to an input imaging region and input image SD may be displayed, together with a simulation image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   a scan unit configured to scan an imaging target region of a subject to be examined with X-rays in accordance with a scan condition;
   a reconstruction unit configured to reconstruct image data on the basis of projection data acquired by the scan;
   a scan condition setting unit configured to set the scan condition;
   a picture quality index calculating unit configured to calculate a value associated with an index of picture quality on the basis of the set scan condition;
   a sample image storage unit configured to store sample image data corresponding to a reference value associated with the index of picture quality;
   a simulation image generating unit configured to generate simulation image data corresponding to the calculated value associated with the index of picture quality from the sample image data on the basis of the calculated value associated with the index of picture quality and the reference value associated with the index of picture quality; and
   a display unit configured to display the generated simulation image data.

2. An apparatus according to claim 1, wherein
   the storage unit stores data associated with a plurality of sample images corresponding to a plurality of reference values, and
   the simulation image generating unit generates the simulation image data by weighting and adding data associated with the plurality of sample images on the basis of the plurality of reference values and calculated values associated with the index of picture quality.

3. An apparatus according to claim 1, wherein
   the storage unit stores data associated with a plurality of sample images corresponding to a plurality of regions, and the simulation image generating unit generates the simulation image data from sample image data corresponding to an imaging target region of the subject.

4. An apparatus according to claim 1, wherein the scan condition includes an image slice thickness, a tube voltage, a tube current, a reconstruction function, and a beam pitch.

5. An apparatus according to claim 4, wherein the picture quality index calculating unit calculates a value associated with the index of picture quality on the basis of at least one of the image slice thickness, the tube voltage, the tube current, the reconstruction function and the beam pitch, and a water equivalent thickness associated with an imaging target region of the subject.

6. An apparatus according to claim 5, further comprising a water equivalent thickness calculating unit configured to calculate the water equivalent thickness on the basis of a body thickness of an imaging target region of the subject.

7. An apparatus according to claim 5, further comprising a water equivalent thickness calculating unit configured to calculate the water equivalent thickness on the basis of scanogram data associated with the subject.

8. An apparatus according to claim 1, further comprising a scan condition storage unit configured to store a plurality of scan conditions corresponding to a plurality of values associated with the index of picture quality, and a scan condition specifying unit configured to specify a scan condition corresponding to a desired value associated with the index of picture quality.

9. An X-ray computed tomography apparatus comprising:
a scan unit configured to scan an imaging target region of a subject to be examined with X-rays;
a reconstruction unit configured to reconstruct image data on the basis of projection data acquired by the scan;
an input unit configured to input a value or dose associated with an index of picture quality;
a simulation image generating unit configured to generate simulation image data corresponding to the input value or dose associated with the index of picture quality; and
a display unit configured to display the generated simulation image data.

10. An apparatus according to claim 9, wherein the input unit includes a slider button to input the value or dose associated with the index of picture quality.

11. An apparatus according to claim 9, wherein the simulation image generating unit generates the simulation image by weighting and adding a plurality of sample images corresponding to a plurality of reference values associated with the index of picture quality on the basis of the plurality of reference values and a calculated value associated with the index of picture quality.

12. An apparatus according to claim 9, wherein the simulation image generating unit generates the simulation image from a plurality of sample images corresponding to the input values or does associated with index of picture quality.

13. An apparatus according to claim 9, further comprising a scan condition recommended value determining unit configured to determine a recommended value of a scan condition corresponding to the input value or dose associated with the index of picture quality.

14. A picture quality simulation apparatus comprising:
a scan condition input unit configured to input a scan condition associated with scanning by an X-ray computed tomography apparatus;
a picture quality index calculating unit configured to calculate an index of picture quality on the basis of the input scan condition;
a sample image storage unit configured to store sample image data corresponding to a reference value associated with the index of picture quality;
a simulation image generating unit configured to generate simulation image data corresponding to the calculated value associated with the index of picture quality from the sample image data on the basis of the calculated value associated with the index of picture quality and a reference value associated with the index of picture quality; and
a display unit configured to display the generated simulation image data.

15. A picture quality simulation apparatus comprising:
an input unit configured to input a value or dose associated with an index of picture quality of an X-ray computed tomography apparatus;
a simulation image generating unit configured to generate simulation image data corresponding to the input value or dose associated with the index of picture quality; and
a display unit configured to display the generated simulation image data.

16. A computer program product configured to store program instructions for execution on a computer system enabling the computer system to perform:
inputting a scan condition associated with an X-ray computed tomography apparatus,
calculating a value associated with an index of picture quality on the basis of the input scan condition;
storing sample image data corresponding to a reference value associated with the index of picture quality,
generating simulation image data corresponding to the calculated value associated with the index of picture quality from the sample image data on the basis of the calculated value associated with the index of picture quality and a reference value associated with the index of picture quality, and
displaying the generated simulation image data.

17. A computer program product configured to store program instructions for execution on a computer system enabling the computer system to perform:
inputting a value or dose associated with an index of picture quality of an X-ray computed tomography apparatus,
generating simulation image data corresponding to the input value or dose associated with index of picture quality, and
displaying the generated simulation image data.

* * * * *

UNITED STATES PATENT AND TRADEMARK OFFICE
CERTIFICATE OF CORRECTION

PATENT NO. : 7,031,423 B2
APPLICATION NO. : 10/830106
DATED : April 18, 2006
INVENTOR(S) : Shinsuke Tsukagoshi Page 1 of 1

It is certified that error appears in the above-identified patent and that said Letters Patent is hereby corrected as shown below:

On the title page, Item (73), the Assignee. Item (73) should read:

(73) Assignees: Kabushiki Kaisha Toshiba, Tokyo (JP)
Toshiba Medical Systems Corporation, Otawara-shi (JP)

Signed and Sealed this

Fourth Day of November, 2008

JON W. DUDAS
*Director of the United States Patent and Trademark Office*